US006980111B2

(12) United States Patent
Nolte

(10) Patent No.: US 6,980,111 B2
(45) Date of Patent: Dec. 27, 2005

(54) MEDICATION TRACKING SYSTEM

(75) Inventor: Myles Dean Nolte, Sanford, NC (US)

(73) Assignee: Hill-Rom Services, Inc., Wilmington, DE (US)

( * ) Notice: Subject to any disclaimer, the term of this patent is extended or adjusted under 35 U.S.C. 154(b) by 218 days.

(21) Appl. No.: 10/211,187

(22) Filed: Aug. 2, 2002

(65) Prior Publication Data

US 2003/0048187 A1 Mar. 13, 2003

Related U.S. Application Data

(60) Provisional application No. 60/309,963, filed on Aug. 3, 2001.

(51) Int. Cl.[7] ................................................ G08B 13/14
(52) U.S. Cl. ................ 340/572.8; 340/5.92; 340/545.6
(58) Field of Search ......................... 340/572.1, 573.1, 340/545.6, 686.4, 5.92, 568.1, 572.8, 572.9; 705/28; 235/385

(56) References Cited

U.S. PATENT DOCUMENTS

| | | | |
|---|---|---|---|
| 3,439,320 A | 4/1969 | Ward | |
| 3,739,329 A | 6/1973 | Lester | |
| 4,151,407 A | 4/1979 | McBride et al. | |
| 4,216,462 A | 8/1980 | McGrath et al. | |
| 4,225,953 A | 9/1980 | Simon et al. | |
| 4,275,385 A | 6/1981 | White | |
| 4,601,064 A | 7/1986 | Shipley | |
| 4,649,385 A | 3/1987 | Aires et al. | |
| 4,756,706 A | 7/1988 | Kerns et al. | |
| 4,785,969 A | 11/1988 | McLaughlin | |
| 4,837,568 A | 6/1989 | Snaper | |
| 4,967,195 A | 10/1990 | Shipley | |
| 4,990,892 A | 2/1991 | Guest et al. | |
| 5,027,314 A | 6/1991 | Linwood et al. | |
| 5,051,741 A | 9/1991 | Wesby | |
| 5,062,151 A | 10/1991 | Shipley | |
| 5,119,104 A | 6/1992 | Heller | |
| 5,153,584 A | 10/1992 | Engira | |
| 5,218,344 A | 6/1993 | Ricketts | |
| 5,291,399 A | 3/1994 | Chaco | |
| 5,317,309 A | 5/1994 | Vercellotti et al. | |
| 5,319,363 A | 6/1994 | Welch et al. | |
| 5,363,425 A | 11/1994 | Mufti et al. | |
| 5,387,993 A | 2/1995 | Heller et al. | |
| 5,390,238 A | 2/1995 | Kirk et al. | |
| 5,396,224 A | 3/1995 | Dukes et al. | |
| 5,402,469 A | 3/1995 | Hopper et al. | |
| 5,417,222 A | 5/1995 | Dempsey et al. | |
| 5,426,425 A | 6/1995 | Conrad et al. | |
| RE35,035 E | 9/1995 | Shipley | |
| 5,455,851 A | 10/1995 | Chaco et al. | |
| 5,458,123 A | 10/1995 | Unger | |
| 5,465,082 A | 11/1995 | Chaco | |
| 5,471,404 A | 11/1995 | Mazer | |

(Continued)

FOREIGN PATENT DOCUMENTS

GB 2 193 359 2/1988

(Continued)

OTHER PUBLICATIONS

"Great New Product: Infrared Locator," Teleconnect, Feb., 1986.

(Continued)

*Primary Examiner*—Thomas Mullen
(74) *Attorney, Agent, or Firm*—Bose McKinney & Evans LLP

(57) ABSTRACT

An apparatus and method for determining the location of a medication container, such as an intravenous bag.

34 Claims, 8 Drawing Sheets

U.S. PATENT DOCUMENTS

| | | |
|---|---|---|
| 5,493,283 A | 2/1996 | Hopper et al. |
| 5,515,426 A | 5/1996 | Yacenda et al. |
| 5,527,289 A | 6/1996 | Foster et al. |
| 5,534,876 A | 7/1996 | Erikson et al. |
| 5,536,084 A | 7/1996 | Curtis et al. |
| 5,541,585 A | 7/1996 | Duhame et al. |
| 5,548,637 A | 8/1996 | Heller et al. |
| 5,561,412 A | 10/1996 | Novak et al. |
| 5,572,195 A | 11/1996 | Heller et al. |
| 5,576,952 A | 11/1996 | Stutman et al. |
| 5,588,009 A | 12/1996 | Will |
| 5,593,390 A | 1/1997 | Castellano et al. |
| 5,594,786 A | 1/1997 | Chaco et al. |
| 5,627,524 A | 5/1997 | Fredrickson et al. |
| 5,633,742 A | 5/1997 | Shipley |
| 5,647,491 A | 7/1997 | Foster et al. |
| 5,651,775 A | 7/1997 | Walker et al. |
| 5,689,229 A | 11/1997 | Chaco et al. |
| 5,699,038 A | 12/1997 | Ulrich et al. |
| 5,742,233 A | 4/1998 | Hoffman et al. |
| 5,781,442 A * | 7/1998 | Engleson et al. ........... 700/214 |
| 5,788,851 A | 8/1998 | Kenley et al. |
| 5,822,544 A | 10/1998 | Chaco et al. |
| 5,838,223 A | 11/1998 | Gallant et al. |
| 5,842,976 A | 12/1998 | Williamson |
| 5,852,590 A | 12/1998 | de la Huerga |
| 5,910,776 A * | 6/1999 | Black ...................... 340/572.1 |
| 5,925,021 A | 7/1999 | Castellano et al. |
| 5,954,641 A | 9/1999 | Kehr et al. |
| 5,980,501 A | 11/1999 | Gray |
| 6,004,020 A | 12/1999 | Bartur |
| 6,032,155 A | 2/2000 | de la Huerga |
| 6,102,855 A | 8/2000 | Kehr et al. |
| 6,112,182 A | 8/2000 | Akers et al. |
| 6,150,942 A | 11/2000 | O'Brien |
| 6,155,603 A | 12/2000 | Fox |
| 6,202,923 B1 | 3/2001 | Boyer et al. |
| 6,219,587 B1 | 4/2001 | Ahlin et al. |
| 6,249,717 B1 | 6/2001 | Nicholson et al. |
| 6,260,761 B1 | 7/2001 | Peoples, Jr. |
| 6,263,259 B1 | 7/2001 | Bartur |
| 6,285,285 B1 * | 9/2001 | Mongrenier ............. 340/572.1 |
| 6,304,797 B1 | 10/2001 | Shusterman |
| 6,314,384 B1 | 11/2001 | Goetz |
| 6,344,794 B1 | 2/2002 | Ulrich et al. |
| 6,421,650 B1 | 7/2002 | Goetz et al. |
| 6,462,656 B2 | 10/2002 | Ulrich et al. |
| 2002/0067270 A1 * | 6/2002 | Yarin et al. ............... 340/573.1 |
| 2002/0188259 A1 * | 12/2002 | Hickle et al. ................ 604/189 |
| 2003/0006878 A1 * | 1/2003 | Chung ...................... 340/572.1 |
| 2003/0127508 A1 * | 7/2003 | Jones ......................... 235/375 |

FOREIGN PATENT DOCUMENTS

| | | |
|---|---|---|
| GB | 2 230 365 | 10/1990 |
| GB | 2 265 038 | 9/1993 |
| WO | 00/58901 | 10/2000 |

OTHER PUBLICATIONS

T.H. Ooi, "Low Cost RF Identification and Locating System," IEEE Trans. On Consumer Electronics, vol. 35, No. 4, Nov. 1989, pp. 831-839.

United Identifications Systems Corp., Infra-Com, 1989.

"Infra-Com® Patient Tracking System", Developed by United Identification Systems Corp., 2 pgs.

"Keeping Track of Alzheimer and Dementia Prone Patients Just Got Easier", Sycon, 6 pages.

Sekurmed Sales Brochure, 1991.

R.C. Livermore, "Health Service Applications in England and Wales," International Conference and Workshop on Smart Card Applications and Technologies, 1988, pp. 5-eoa.

Brown, Vallbona & Kitasanono, "A New Patient Record System Using the Laser-Card," Optical Information Systems, vol. 8, No. 4, Jul.-Aug. 1988, pp. 156-161.

D. Artusi, "The Technology of Smartcards and Their Applications," Electro/86 and Mini/Micro Northeast Conference, 1986, pp. 1-8.

M.P. Siedband, "Data card system for filmless radiography," Medical Imaging vol. 767, Part 2, pp. 831-833, 1987.

R.G. Stevens, "Experiences with Computer Card Medication Records in Britain," International Conference and Workshop on Smart Card Applications and Technologies, pp. 12-eoa., 1988.

G.B. Latamore, "Smart Cards Get Smarter," High Technology Business, pp. 35-37, Sep. 1987.

G. Moore, "The hospital connection," Computer Systems Europe, pp. 73-76, May 1989.

M. Oikawa, "Marketing Activities in Finland," NTT Review, vol. 1, No. 2, pp. 102-103, 1989.

Executone Infostar brochure, 1993.

* cited by examiner

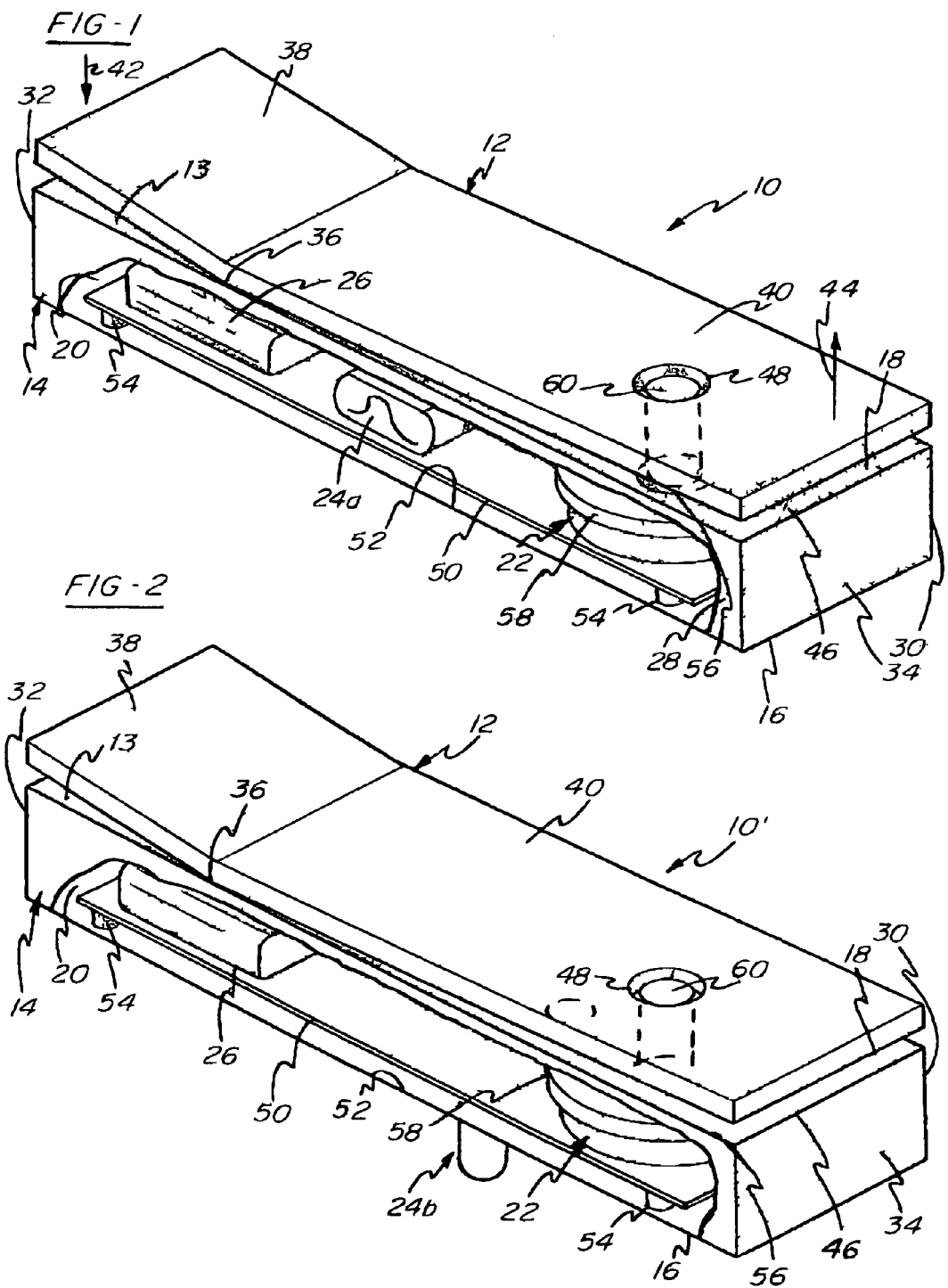

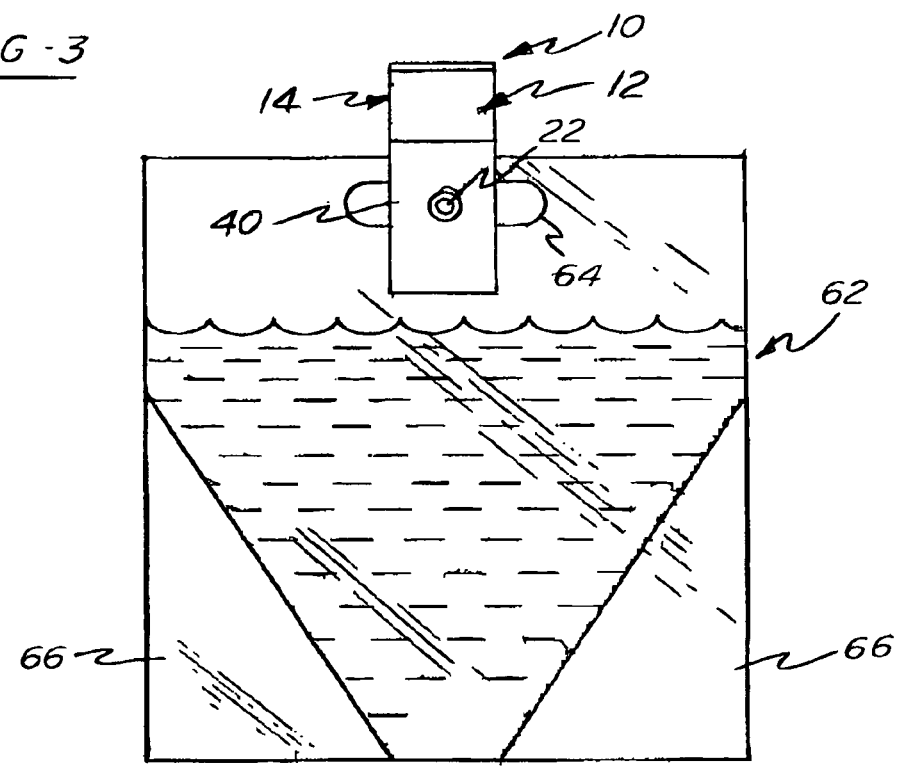
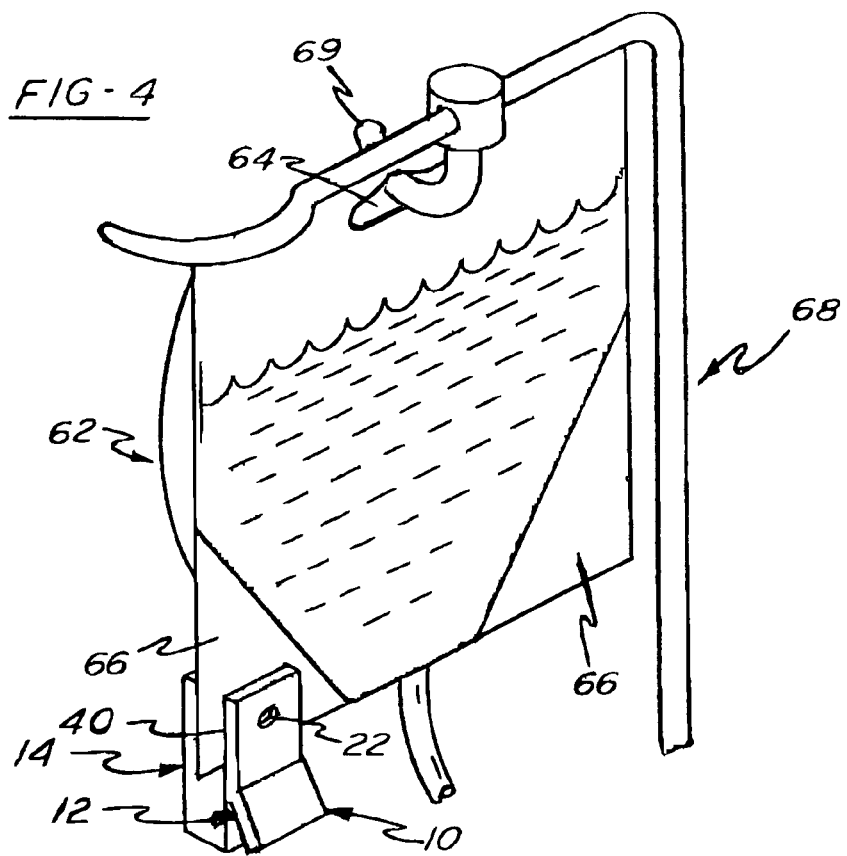

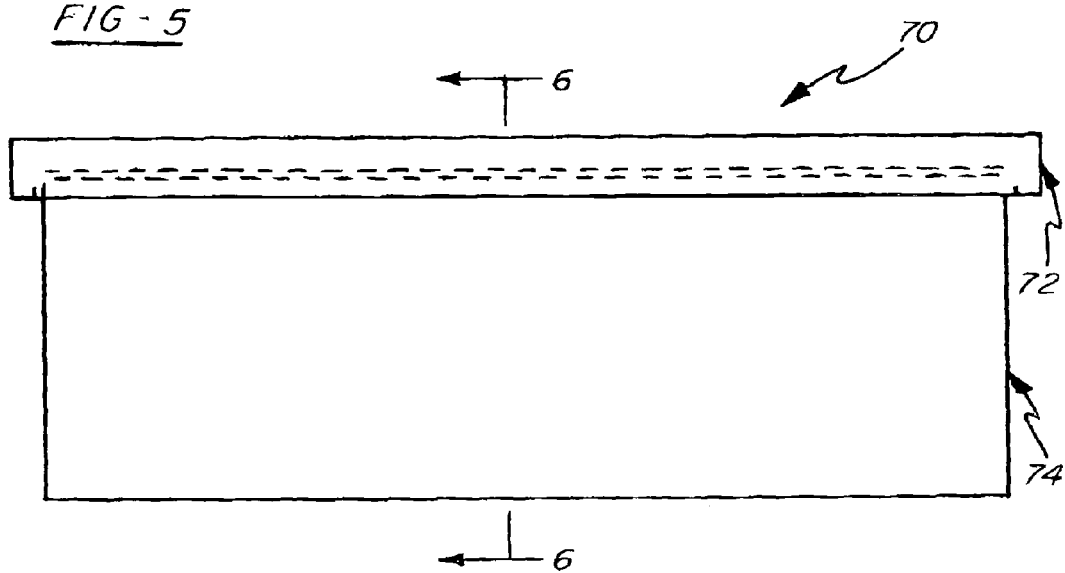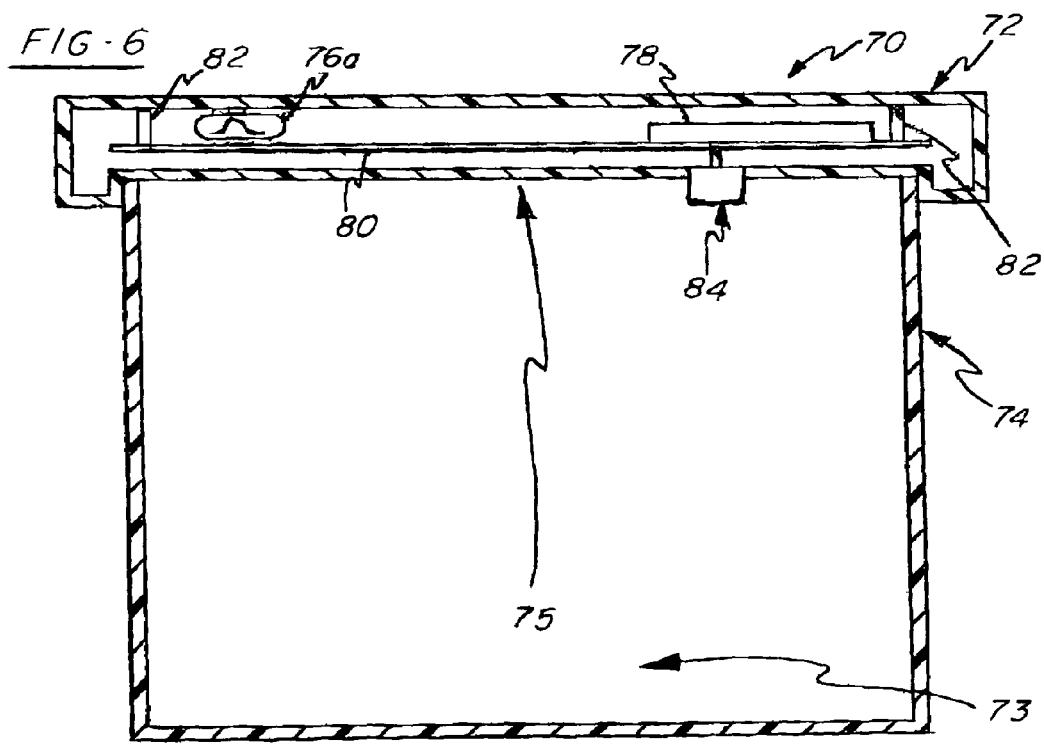

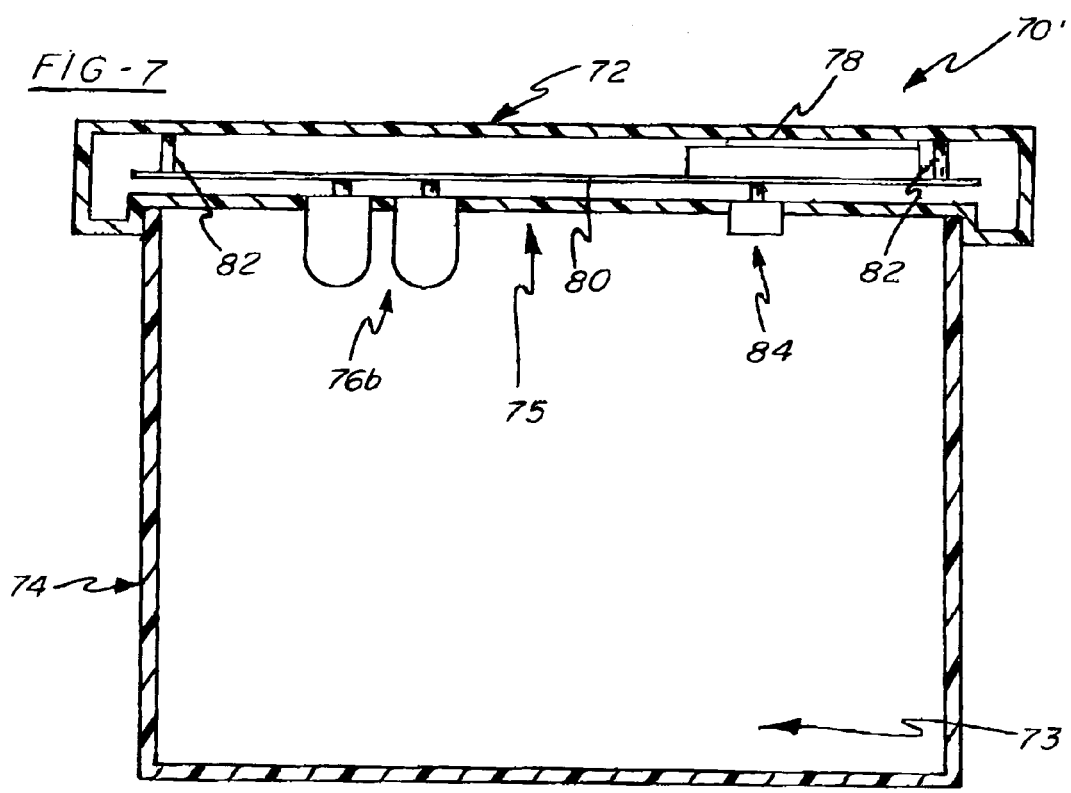
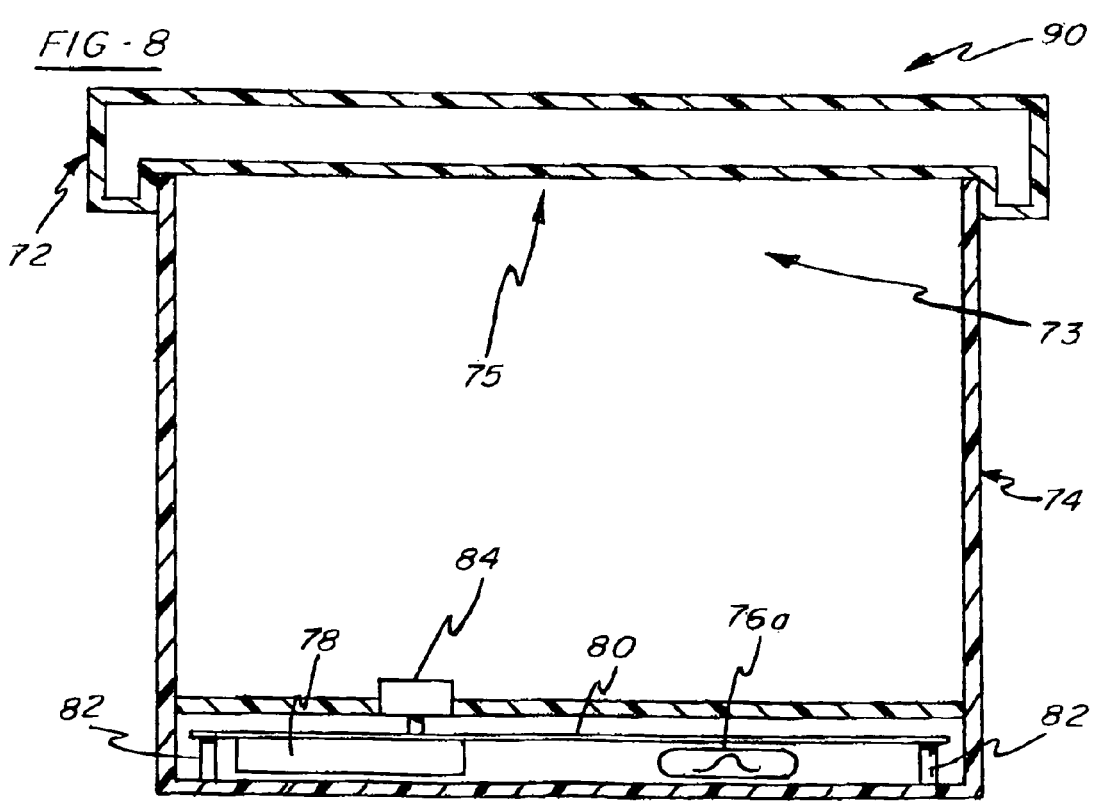

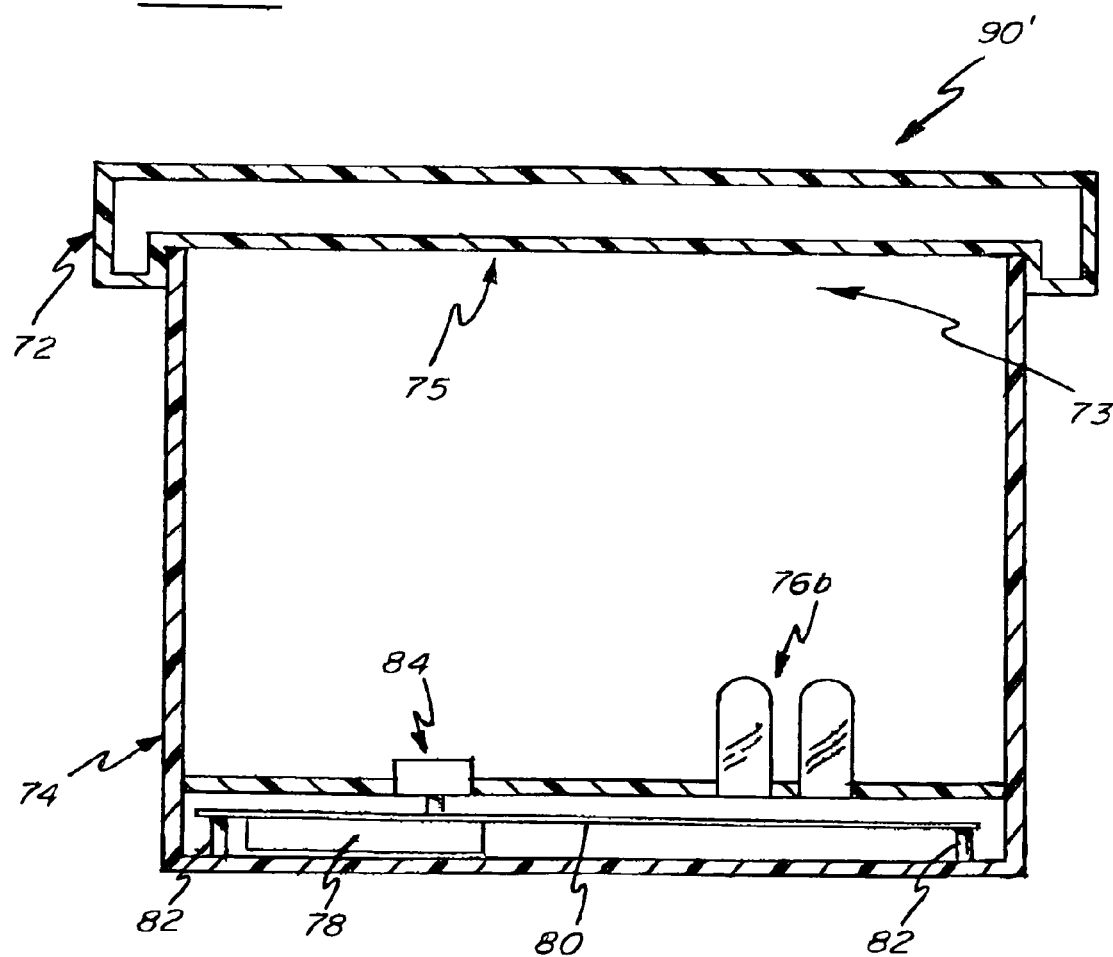

MEDICATION TRACKING SYSTEM

CROSS-REFERENCE TO RELATED APPLICATION

This application claims the benefit of U.S. Provisional Patent Application Ser. No. 60/309,963, filed Aug. 3, 2001, the disclosure of which is expressly incorporated by reference herein.

BACKGROUND AND SUMMARY OF THE INVENTION

The present invention relates generally to an apparatus and method for determining the location of a medication container. More particularly, the present invention relates to an apparatus and method for verifying that medications have been delivered to the proper target destination before they are administered or consumed.

Hospitals distribute medications (or "meds") to their patients on a routine basis. A typical distribution begins with a physician writing a prescription for a particular patient. The prescription is often filled by an in-hospital pharmacy and then picked up from the pharmacy and hand delivered to the patient's room, where the medication is administered to the patient by a doctor, a nurse or other qualified caregiver. In any event, the typical distribution system relies on a human chain of custody to ensure that medications dispensed from the pharmacy eventually are delivered to the correct patients. Therefore, there is a need to verify that medications have been delivered to the proper patient before they are administered or consumed.

The present invention fulfills the above need, among others, by providing an apparatus and method for tracking medications in a hospital. In one illustrative embodiment, the apparatus includes a transmitter and an activation device operably coupled to the transmitter for selectively activating the transmitter. The activation device is configured to deactivate the transmitter when the activation device is secured through a hanging hole in an intravenous bag and is configured to activate the transmitter when the activation device is secured to a solid web tab in the intravenous bag. The apparatus further includes a hanging hole securing device configured to secure the transmitter through the hanging hole formed in the intravenous bag. The apparatus further includes a solid web tab securing device configured to secure the transmitter to a solid web tab of an intravenous bag, wherein the solid web tab securing device is configured to activate the transmitter when the activation device is secured to the solid web tab. Illustratively, the transmitter comprises at least one of an infrared transmitter and a radio frequency transmitter.

In a further illustrative embodiment, the apparatus of the present invention includes a housing having opposing front and rear walls, and defining interior and exterior surfaces. The rear wall includes a housing aperture extending therethrough between the interior and exterior surfaces. A fastener is connected to the exterior surface of the rear wall of the housing and includes a fastener aperture. The apparatus further includes a switch having a base supported by the housing and a crown extendable into both the housing aperture and the fastener aperture. The switch is operable between at least a first position and a second position. A transmitter is operably coupled to the switch, wherein positioning of the switch in the first position deactivates the transmitter and positioning of the switch in the second position activates the transmitter.

Illustratively, the switch is in the first position when the crown extends into both the housing aperture and the fastener aperture, and the switch is in the second position when the crown does not extend into the fastener aperture.

In a further illustrative embodiment, the apparatus of the present invention includes a housing, a transmitter supported by the housing, and an activation device supported by the housing and configured to selectively activate the transmitter. A fastener is supported by the housing and is configured to cooperate with the activation device wherein the fastener causes the activation device to selectively activate the transmitter depending upon the relative position of the fastener on an intravenous bag.

Illustratively, the fastener causes the activation device to deactivate the transmitter when the fastener cooperates with the activation device to secure the housing through a hanging hole of the intravenous bag. Further illustratively, the fastener causes the activation device to activate the transmitter when the fastener secures the housing to a solid web tab of the intravenous bag.

Illustratively, the fastener includes a fastener aperture and the activation device includes a switch having a crown configured to be received within the fastener aperture, the crown of the switch being operable between at least a first position and a second position, the first position causing the transmitter to deactivate and the second position causing the transmitter to activate. In the first position, the crown of the switch passes through the hanging hole of the intravenous bag, and in the second position, the crown of the switch engages the solid web tab of the intravenous bag.

In another illustrative embodiment, the apparatus of the present invention includes a container housing, a lid connected to the container housing for relative movement therewith, and a transmitter operably connected to at least one of the container housing and the lid. An associating device is configured to associate at least one of the container housing and the lid with a target destination.

Illustratively, a switch is operably coupled to the transmitter and is configured to selectively activate the transmitter. The switch may comprise a photosensor configured to be actuated by ambient light.

Further illustratively, the apparatus comprises a verification device configured to verify that the target designation equals an actual destination of the medication container.

In another illustrative embodiment of the present invention, a method is provided which includes the steps of tagging medications, associating a tracking device with a target destination, delivering the tagged medications to an actual destination, activating the tracking device, and verifying that the actual destination is the target destination. The step of associating may be implemented through software communicating with hardware via a bar code, a radio frequency (RF) communication, or an infrared (IR) communication.

An alternative illustrative embodiment of the method includes the steps of tagging the medications, activating a tracking device, associating the tracking device with a target destination, tracking the tagged medications to an actual destination, and verifying that the actual destination is the target destination. Again, the step of associating may be implemented through software communicating with hardware, a bar code, an RF communication, or an IR communication.

The features and advantages of the present invention described above, as well as additional features and advantages, will be readily apparent to those skilled in the art upon reading the following detailed description and referring to the accompanying drawings.

BRIEF DESCRIPTION OF THE DRAWINGS

FIG. 1 is a perspective view, with a partial cut-away, of an intravenous bag tracking device according to a first illustrative embodiment of the present invention;

FIG. 2 is a perspective view, with a partial cut-away, of an intravenous bag tracking device according to a second illustrative embodiment of the present invention;

FIG. 3 is a side elevational view of the intravenous bag tracking device of the present invention attached to an intravenous bag in an inactive mode;

FIG. 4 is a perspective view of the intravenous bag tracking device of the present invention attached to an intravenous bag in an active mode;

FIG. 5 is a side elevational view of a medication container tracking device according to an illustrative embodiment of the present invention;

FIG. 6 is a cross-sectional view of a medication container tracking device, taken along line 6—6 of FIG. 5;

FIG. 7 is a cross-sectional view similar to FIG. 6 illustrating another illustrative embodiment medication container tracking device of the present invention;

FIG. 8 is a cross-sectional view similar to FIG. 6 illustrating a further illustrative embodiment medication container tracking device of the present invention;

FIG. 9 is a cross-sectional view similar to FIG. 6 illustrating another illustrative embodiment medication container tracking device of the present invention;

DETAILED DESCRIPTION OF THE INVENTION

Figure 10:
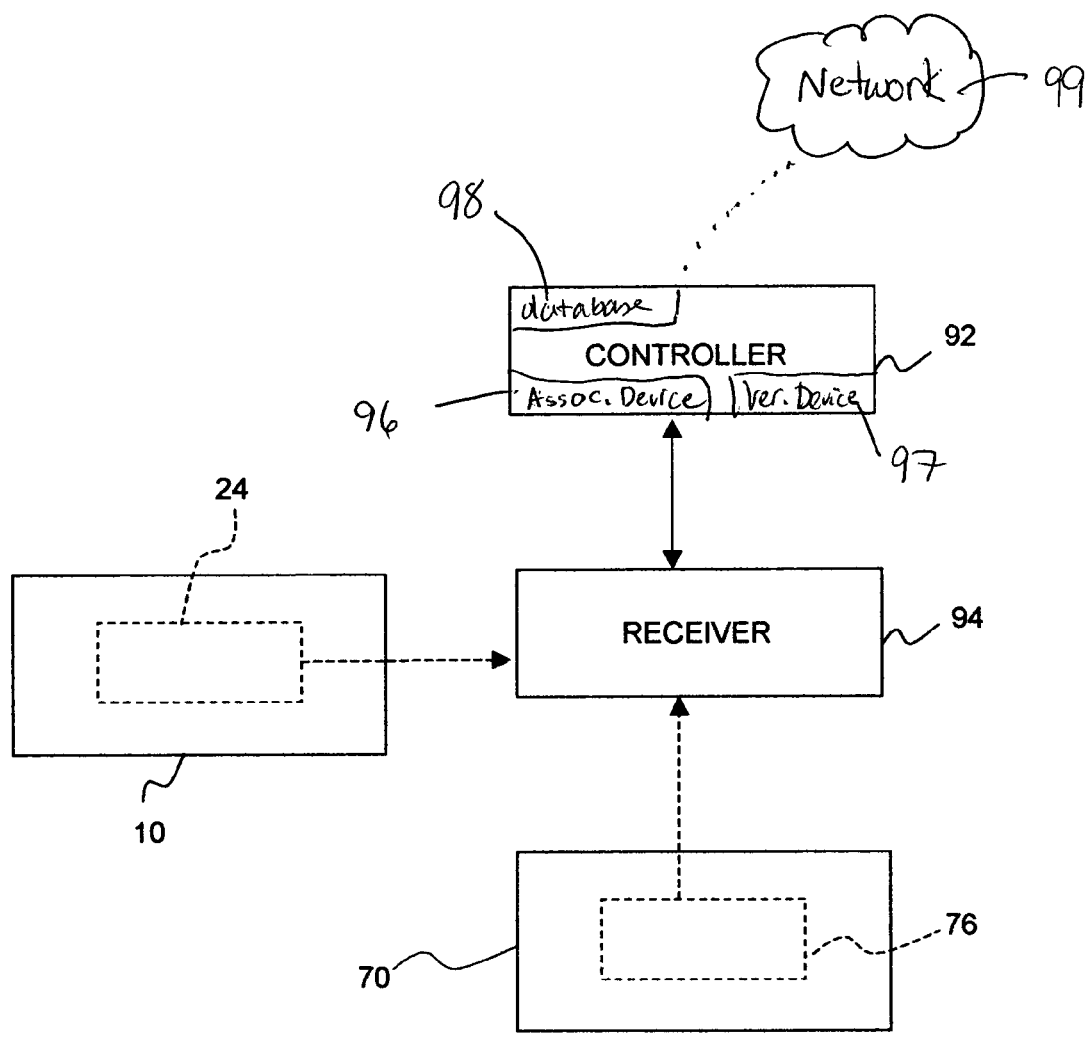
FIG. 10 is a block diagram illustrating interaction of tracking devices of the present invention with a controller.

FIG. 1 illustrates an intravenous bag tracking device 10 according to a first exemplary embodiment of the present invention. The intravenous bag tracking device 10 includes a fastener 12 connected to an outer surface 13 of a housing 14. The housing 14 includes opposing front and rear walls 16 and 18 which define a chamber 20 therebetween for receiving a switch 22, a transmitter 24a, and a battery 26.

The housing 14 may further include a pair of opposing side walls 28, 30 connected to a pair of opposing end walls 32, 34 and to the front and rear walls 16 and 18, thereby fully enclosing the chamber 20. As may be readily appreciated, an access panel or door (not shown) may be provided to facilitate access to the chamber 20 as needed, for example, to replace the battery 26.

The fastener 12 is illustratively pivotally connected to the rear wall 18 of the housing 14 by a hinge 36. The fastener 12 includes a grip portion 38 and a clamp portion 40 separated by the hinge 36. The hinge 36 is configured to permit movement of the fastener 12 between first and second positions. In the first, or relaxed, position the clamp portion 40 is biased toward the outer surface 13 of the rear wall 18.

As may be appreciated, by applying force to the grip portion 38 in the direction of arrow 42, the fastener 12 is placed in its second, or extended, position where the clamp portion 40 moves away from the rear wall 18 in the direction of arrow 44, thereby creating an access slot 46 therebetween. Release of the grip portion 38 causes the clamp portion 40 to return to its clamped first position as biased toward the rear wall 18, and thereby clamping an object within the access slot 46 to the rear wall 18 of the housing 14.

The fastener 12 is illustratively formed of a resilient material to cause the clamp portion 40 to be biased toward the rear wall 18. Moreover, the hinge 36 is illustratively a self-resilient spring biased hinge, a glue bond, a weld, or other suitable connector. Alternatively, a biasing member, such as a spring (not shown), may be operably connected to the fastener 12 for biasing the clamp portion 40. An aperture 48 is formed within, and extends through, the clamp portion 40 of the fastener 12.

A controller, such as a printed circuit board 50, is supported within the chamber 20. The circuit board 50 is secured to an inner surface 52 of the housing 14 through a plurality of mounting posts 54. The mounting posts 54 may be integrally formed with the front wall 16 of the housing 14 and secured to the circuit board 50 through conventional fasteners, such as screws (not shown), although other fastening means, such as glue bonds, rivets or welds, may be readily substituted therefor.

The hinge 36 connects the fastener 12 to the rear wall 18 of the housing 14 such that the aperture 48 of the fastener 12 is substantially coaxially aligned with an aperture 56 formed within the rear wall 18 of the housing 14. The switch 22 is illustratively a normally-open push-button type and includes a base 58 supporting a crown 60 for relative movement therebetween. The base 58 is illustratively soldered or otherwise operably coupled to the circuit board 50, such that the crown 60 extends through the aperture 56 of the housing 14 and is at least partially received within the aperture 48 of the fastener 12. Moreover, the crown 60 illustratively extends outwardly beyond the outer surface 13 of the housing 14 and into the access slot 46 for engaging objects received therein.

While in the illustrative embodiments detailed herein the switch 22 is of a mechanical push-button type, it should be appreciated that other types of switches capable of detecting an object in the access slot 46 may be substituted therefor, including photosensors and proximity switches.

The transmitter 24 of FIG. 1 comprises a radio frequency ("RF") transmitter 24a which is soldered or otherwise electrically connected to the circuit board 50. The circuit board 50, in turn, is configured to electrically connect or couple the RF transmitter 24a to the switch 22 to selectively transmit RF signals or waves. When the switch 22 is depressed, the RF transmitter 24a transmits and when the switch 22 is not depressed, the RF transmitter 24a does not transmit. The RF transmitter 24a may comprise an antenna coil or one of any conventional RF transmitters readily available on the market.

Illustratively, the battery 26 is soldered or otherwise suitably connected to the printed circuit board 50. The battery 26 is operable to provide electrical power to the tracking device 10 and may suitably be of either a rechargeable type or a non-rechargeable type. In either case, the battery 10 is of a type readily available on the market.

Referring now to FIG. 2, an alternative embodiment tracking device 10' is illustrated as being substantially identical to the tracking device 10 of FIG. 1. The only substantial difference between these embodiments is that the transmitter 24 of the tracking device 10' is an infrared ("IR") transmitter 24b as opposed to the RF transmitter 24a. The IR transmitter 24b is soldered or otherwise electrically connected to the printed circuit board 50. The circuit board 50 is configured to electrically connect or, in turn, couple the IR transmitter 24b to the switch 22. In conjunction with the switch 6, the IR transmitter 10 is operable to selectively transmit IR signals or waves. When the switch 22 is depressed, the IR transmitter 24b transmits and when the switch 22 is extended (not depressed), the IR transmitter 24b does not transmit. The IR transmitter 24b may comprise light emitting diodes (LED's) or any conventional IR transmitter readily available on the market.

It should be further noted that the RF transmitter 24a may be used in combination with the IR transmitter 24b in a single intravenous tracking device 10.

Referring now to FIGS. 3 and 4, the operation of the intravenous bag tracking device 10 is described in greater detail. When a pharmacist dispenses a conventional intravenous bag 62 from a hospital pharmacy, the pharmacist fastens the housing 14 of the intravenous bag tracking device 10 thereto. More particularly, the switch 22 of the tracking device 10 is positioned to pass through the hanging hole 64 of the intravenous bag 62, and the clamp portion 40 of the fastener 12 clamps to the intravenous bag 62 adjacent the hole 64 thereby securing the tracking device 10 to the intravenous bag 62. While the switch 22 is fastened through the hanging hole 64, the crown 60 is extended, and thus, the transmitter 24 is inactive and therefore does not transmit signals. FIG. 3 illustrates the intravenous bag tracking device 10 attached to the intravenous bag 62 in the inactive mode.

After the intravenous bag 62 is delivered to a patient room, a nurse or other appropriate caregiver moves the housing 14 of the intravenous bag tracking device 10 from the hanging hole 64 to a solid web tab 66 of the intravenous bag 62. More particularly, the web tab 66 is positioned within the access slot 46 defined by moving the clamp portion 40 of the fastener 12 away from the rear wall 18, in the direction of arrow 44 of FIG. 1, by forcing the grip portion 38 toward the housing 14, in the direction of arrow 42 of FIG. 1. Once the web tab 66 is thus positioned, the grip portion 38 is released thereby returning the fastener 12 to the first, or relaxed, position where the fastener 12 secures the web tab 66 between the clamp portion 40 and the rear wall 18. As such, the switch 22 is depressed against the solid web tab 66, thereby activating the transmitter 24 which, in turn, transmits signals. FIG. 4 illustrates the intravenous bag tracking device 10 attached to the intravenous bag 62 in the active mode. In a conventional manner, the intravenous bag 62 is supported by an intravenous pole 68 by passing a hook 69 through the hanging hole 64. Further operations of the intravenous bag tracking device 10 are discussed below in connection with FIGS. 11 and 12.

FIG. 5 is a side elevational view of a medication container tracking device 70 according to a further exemplary embodiment of the present invention. FIG. 6 illustrates a cross-sectional view of a first embodiment medication container tracking device 70, taken along line 6-6 of FIG. 5. Meanwhile, FIG. 7 illustrates a cross-sectional view, similar to that of FIG. 6, of a second embodiment medication container tracking device 70'. The medication container tracking device 70 illustratively includes a cover or lid 72, a container housing 74, a transmitter 76, a battery 78, a printed circuit board 80, mounting posts 82, and a switch 84. The lid 72 is connected to the respective container housing 74 for relative movement therewith. More particularly, the lid 72 is illustratively supported for at least partial removal from the container housing 74 thereby providing access to an interior chamber 73 through an opening 75. It should be recognized that the lid 72 may be hingedly connected to the container housing 74.

The transmitter 76, the battery 78, the printed circuit board 80, and the mounting posts 82 are configured and assembled in manners like those discussed above in connection with the embodiments of FIGS. 1 and 2. However, while the switch 84 may be a normally-open push-button type like switch 22 above, switch 84 is preferably of a photosensor type. To this end, in the exemplary embodiments described herein, the switch 84 may comprise one of a wide variety of photosensitive devices readily available on the market. Accordingly, when the switch 84 is actuated by ambient light, such as when the lid 72 is open or at least partially removed from the container housing 74 and thereby allowing light to pass therebetween, the transmitter 76 transmits signals or waves. Likewise, when the switch 84 is not actuated by ambient light, such as when the lid 72 is closed or concealing the inner chamber 73 of the housing 74, the transmitter 76 does not transmit. It may be appreciated that other suitable switches capable of detecting an open condition of the lid 72, such as contact switches and proximity sensors, may be readily substituted for the photosensor switch 84.

The transmitter 76 may comprise an RF transmitter 76a or an IR transmitter 76b in the manner described above with respect to FIGS. 1 and 2. FIGS. 6 and 8 illustrate embodiments of the medication container tracking device 70 and 90 including the RF transmitter 76a, while FIGS. 7 and 9 illustrate alternative embodiments of the medication container tracking device 70' and 90' including the IR transmitter 76b.

In alternative embodiments of the tracking device 70, 70' and 90, 90', the switch 84 and/or the transmitter 76 may be suitably mounted so that they are supported by, and substantially flush with, the lid 72 (FIGS. 6 and 7) or the medication container housing 74 (FIGS. 8 and 9). The switch 84 and transmitter 76 may be covered by a transparent surface (not shown) for protection and/or to provide an even surface area within the medication container housing 74.

The medication container tracking device 70 is operated in the following manner. When a pharmacist dispenses medication from the hospital pharmacy, the pharmacist removes the lid 72 from the medication container housing 74, puts the medication into the medication container housing 24, and then puts the lid 72 back onto the medication container housing 74 thereby concealing the inner chamber 73.

While the lid 72 is removed, the switch 84 is activated by ambient light, and in response, the transmitter 76 transmits signals. While the lid 72 is positioned on the medication container housing 74 and closing the opening 75, the switch 84 is not activated by ambient light, and thus, the transmitter 76 does not transmit signals.

After the medication is delivered to a patient room, a nurse or other appropriate caregiver removes the lid 72 from the medication container housing 74 in order to gain access to the medications, thereby placing the medication container tracking device 70 in the active mode. After the medications are administered or consumed, the nurse or other appropriate caregiver puts the lid 72 back on the medication container housing 74. As such, the medication container tracking device 70 is again in the inactive mode. Further operations of the medication container tracking device 70 are discussed below in connection with FIGS. 10–12.

FIG. 10 is a block diagram illustrating the basic interaction of the intravenous bag tracking device 10 and the medication container tracking device 70 with a remote controller 92. When the tracking devices 10 and 70 are placed in an active mode in the manner detailed above, the respective transmitters 24 and 76 send wireless signals to a receiver 94 typically located within the patient's room. The receiver 94, in turn, sends a signal to the controller 92 indicating receipt of the signal from the respective transmitter 24 or 76. The controller 92 may comprise a conventional computer processing unit including a database 98 an associating device 96, a verifying device 97, and/or a network 99.

Figure 11:
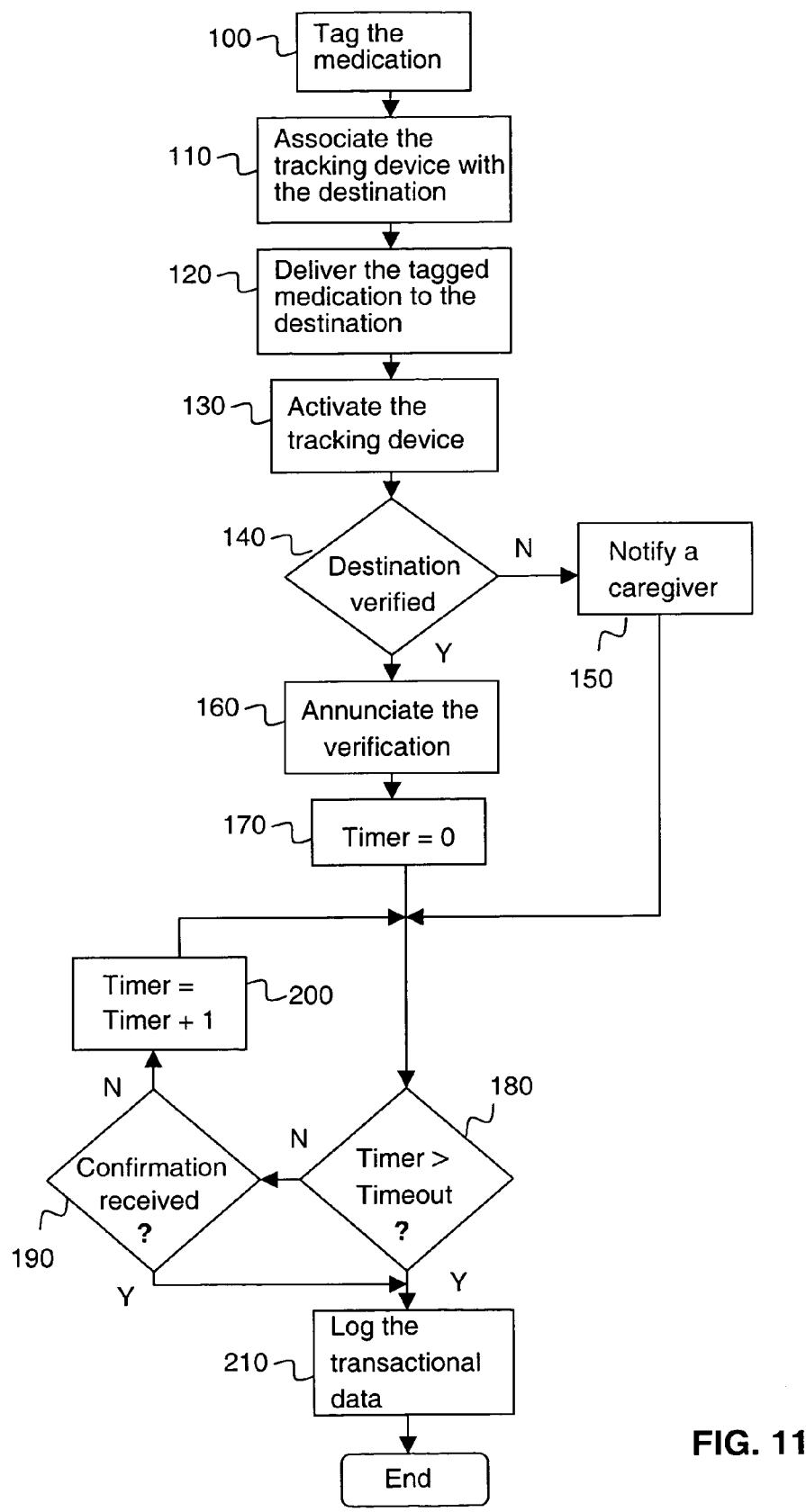
FIG. 11 is a flow diagram illustrating a first method for logging transactional data regarding the delivery of medication to a patient according to an illustrative embodiment of the present invention.

FIG. 11 is a flow diagram illustrating a first method of logging transactional data regarding the delivery of medication to a patient according to an exemplary embodiment of the present invention. Step 100 represents tagging the meds where a tracking device (which may be the intravenous bag tracking device 10 or the medication container tracking device 70, 90 respectively, discussed above, or any other suitable tracking device) is physically linked with the medication. For example, a pharmacist fastens the housing 14 of the intravenous bag tracking device 10 such that the switch 22 passes through the hanging hole 64 of the intravenous bag 62 (thereby placing the intravenous bag tracking device 10 in the inactive mode); or the pharmacist places medications inside the medication container tracking device 70, 90 and closes the lid 72 (thereby placing the medication container tracking device 70, 90 in the inactive mode).

In step 110, the tracking device 10 or 70, 90 is logically associated with an intended or target destination. The target destination is illustratively the location or area to which the medications are to be delivered and may be, for example, a particular patient's room, an operating room where the patient is to be treated, or even a storage area or closet. For example, to associate the tracking device 10 or 70, 90 with the target destination, a pharmacist may suitably scan bar coded information on the tracking device 10 or 70, 90 into the computer database of the controller 92 and then manually type in the target destination, or the pharmacist may temporarily activate the tracking device 10 or 70, 90 while manually typing in the target destination. Alternatively, a preprogrammed radio frequency identification (RFD) tag may be affixed to the tracking device 10 or 70, 90. An illustrative RFID tag system is disclosed in pending U.S. patent application Ser. No. 09/849,580, filed May 4, 2001, U.S. patent application Ser. No. 10/211,451 entitled "PATIENT POINT-OF-CARE COMPUTER SYSTEM", filed concurrently herewith, and U.S. Provisional Application Ser. No. 60/310,092, filed Aug. 3, 2001, both of which are assigned to the assignee of the present invention and are expressly incorporated by reference herein. In any event, the logical association involves making a record that the medications are intended for the target destination. To this end, it should be readily appreciated that the association may be suitably accomplished via a software database or other software, alteration of firmware, or any other suitable manner.

As detailed below, the tracking device 10 or 70, 90 may be associated with objects other than the above described intended or target destination. For example, the tracking device 10 or 70, 90 may be associated with a patient or caregiver.

In step 120, the medications are delivered to a particular location or actual destination. In step 130, the tracking device 10 or 70, 90 is activated as discussed above in connection with the operation of the intravenous bag tracking device 10 or the medication container tracking device 70, 90. A signal is sent by the respective transmitter 24 or 76 to the receiver 94 which, in turn, sends information to the controller 92.

In step 140, a determination is made by the controller 92 as to whether the actual destination to which the medications arrived is equal to the target destination (that is, whether the destination is verified) by comparing the location of the tracking device to the logical association record made in step 110. Accordingly, it should be readily appreciated that the present invention may be used with the COMposer® communications system available from Hill-Rom, details of which are disclosed in U.S. Pat. Nos. 5,561,412; 5,699,038; and 5,838,223; all of which are expressly incorporated by reference herein. The COMposer® communications system utilizes free-space infrared data transmission from badges and/or tags to receivers in the wall or ceiling. However, it should be noted that the invention is not limited to use with the COMposer® communication system, and that other systems may be substituted therefor.

If the actual destination is not verified as equal to the target destination, then a caregiver is notified by the controller 92 at step 150 that the verification was negative. The caregiver may elect to confirm the notification, which is received at block 190. A timer subroutine is provided as indicated by blocks 180 and 200. When the timer exceeds a predetermined value, as indicated at block 180, the process continues to block 210. Likewise, if the confirmation from the caregiver is received at block 190, the process continues to block 210. It should be readily appreciated that the notification step 150 may be provided by a page, a local or general alarm, or any other suitable hospital notification, including but not limited to those provided by the COMposer® communication system identified above.

If the destination is verified as positive then the verification is annunciated at step 160 and the timer is reset to zero at block 170. Confirmation is received from the caregiver at step 180. As detailed above, if the timer exceeds a predetermined value at block 180, then the process continues at block 210. Likewise, if the caregiver confirms the annunciation then the process proceeds to block 210. It should be readily appreciated that the annunciation of step 160 may suitably be provided by a page, a local or general alarm, or any other suitable hospital notification, including but not limited to those provided by the COMposer® communication system identified above.

At block 210, transactional data, including the (i) status of the verification (negative or positive), and (ii) whether the caregiver confirmed the notification or annunciation, are logged or stored.

Figure 12:
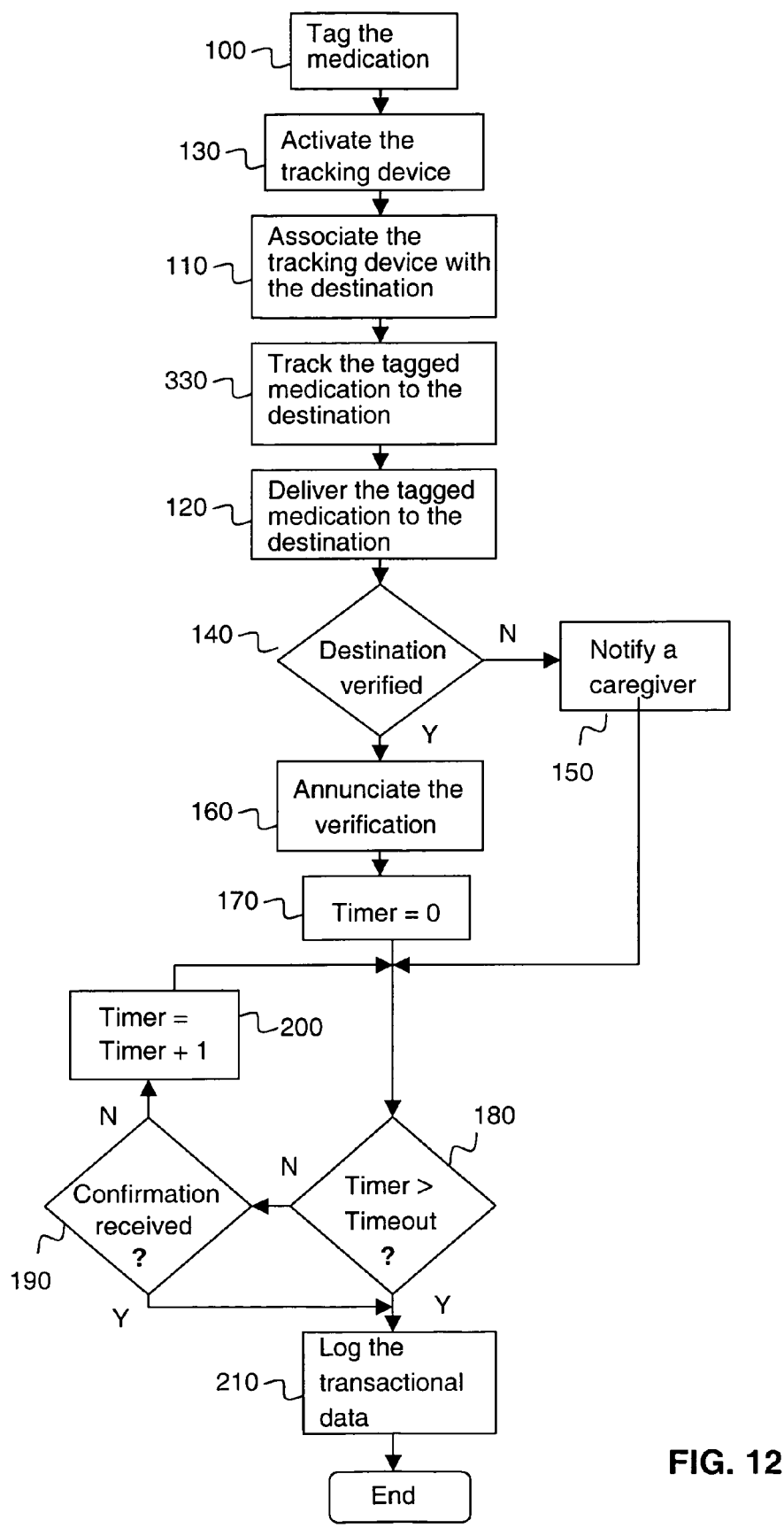
FIG. 12 is a flow diagram illustrating a second method for logging transactional data regarding the delivery of medication to a patient according to another illustrative embodiment of the present invention.

FIG. 12 is a flow diagram illustrating an alternative method of logging transactional data regarding the delivery of medications to a patient. The method of FIG. 12 is substantially identical to the method of FIG. 11 except for the relocation of process block 130 and the addition of process block 330. Block 130 representing the activation of the tracking device 10 or 70, 90 occurs immediately after the medications are tagged at block 100. In block 330, the tagged medications are tracked to the location to which they are actually delivered by receiving transmission signals from the tracking device 10 or 70, 90 as they are transported through the hospital. As such, continuous monitoring of the medications is provided.

As described above, the association step 110 of FIGS. 11 and 12 may associate the tracking device 10 or 70, 90 with objects other than the previously identified intended or target destination. Moreover, the tracking device 10 or 70, 90 may be associated with, for example, a medication type, a medication schedule, a patient, or a caregiver. By associating the tracking device 10 or 70, 90 with a medication type or a medication schedule, a caregiver may verify the proper type of medication, amount of medication and timing of dosages. Similarly, by associating the tracking device 10 or 70, 90 with a patient or a caregiver, it may be ensured that the appropriate patient is supplied with the proper medication distributed only by an authorized caregiver. Additional details regarding these further embodiments are provided in U.S. patent application Ser. No. 10/211,451 entitled "PATIENT POINT-OF-CARE COMPUTER SYSTEM", filed concurrently herewith, and U.S. Provisional Application Ser. No. 60/310,092, filed Aug. 3, 2001, both of which are expressly incorporated by reference herein.

Although the invention has been described in detail with reference to certain illustrated embodiments, variations and modifications exist within the scope and spirit of the present invention as described and defined in the following claims.

What is claimed is:

1. An apparatus for tracking medications contained within an intravenous bag, said apparatus comprising:
   a transmitter;
   an activation device operably coupled to said transmitter; and
   said activation device being configured to deactivate said transmitter when said activation device is secured through a hanging hole formed in an intravenous bag, and said activation device being further configured to activate said transmitter when said activation device is secured to a solid web tab in the intravenous bag.

2. The apparatus of claim 1, further comprising:
   a hanging hole securing device configured to secure said transmitter through the hanging hole in the intravenous bag; and
   a web tab securing device configured to secure said transmitter to the solid web tab of the intravenous bag, said solid web tab securing device being configured to activate said transmitter when said activation device is secured to the solid web tab.

3. The apparatus of claim 2, wherein said activation device includes a switch, said switch including a crown defining said hanging hole securing device.

4. The apparatus of claim 3, wherein said web tab securing device includes a fastener having a clamp portion configured to clamp the solid web tab of the intravenous bag and simultaneously cause said switch to activate said transmitter.

5. The apparatus of claim 1, wherein said transmitter comprises at least one of an infrared transmitter and a radio frequency transmitter.

6. An apparatus for tracking medications, said apparatus comprising:
   a housing including front and rear walls and a housing aperture extending within said rear wall, said housing further including interior and exterior surfaces;
   a fastener connected to said exterior surface of said housing, said fastener including a fastener aperture;
   a switch including a base supported by said housing and a crown extendable into both said housing aperture and said fastener aperture, said switch being operable between at least a first position and a second position; and
   a transmitter operably coupled to said switch;
   wherein placement of said switch in said first position causes said transmitter to deactivate and placement of said switch in said second position causes said transmitter to activate.

7. The apparatus of claim 6, wherein said switch is in said first position when said crown extends into both said housing aperture and said fastener aperture and said switch is said second position when said crown does not extend into said fastener aperture.

8. An intravenous bag locating apparatus comprising:
   a housing;
   a transmitter supported by said housing;
   an activation device supported by the housing and configured to selectively activate said transmitter; and
   a fastener supported by said housing and configured to cooperate with said activation device wherein said fastener causes said activation device to selectively activate said transmitter depending upon the relative position of said fastener on an intravenous bag.

9. The intravenous bag locating apparatus of claim 8, wherein said fastener causes said activation device to deactivate said transmitter when said fastener cooperates with said activation device to secure said housing through a hanging hole of the intravenous bag.

10. The intravenous bag locating apparatus of claim 9, wherein said fastener causes said activation device to activate said transmitter when said fastener secures said housing to a solid web tab of the intravenous bag.

11. The intravenous bag locating apparatus of claim 10, wherein said fastener includes a fastener aperture and said activation device includes a switch having a crown configured to be received within said fastener aperture, said crown of said switch being operable between at least a first position and a second position, said first position causing said transmitter to deactivate and said second position causing said transmitter to activate.

12. The intravenous bag locating apparatus of claim 11, wherein in said first position said crown of said switch passes through the hanging hole of the intravenous bag, and in said second position said crown of said switch engages the solid web tab of the intravenous bag.

13. The intravenous bag locating apparatus of claim 8, wherein said transmitter comprises at least one of an infrared transmitter and a radio frequency transmitter.

14. An apparatus for tracking medications, said apparatus comprising:
   a container housing;
   a lid movably supported by said container housing;
   a transmitter coupled to one of said container housing and said lid, said transmitter being configured to activate in response to movement of one of said container housing and said lid relative to the other of said lid and said container housing; and
   an associating device in communication with said transmitter and configured to associate at least one of said container housing and said lid with a target destination.

15. The apparatus of claim 14, further comprising a switch operably coupled to said transmitter and configured to activate said transmitter automatically in response to movement of said lid relative to said container housing.

16. The apparatus of claim 15, wherein said switch comprises a photosensor configured to be activated by ambient light.

17. The apparatus of claim 14, wherein said transmitter comprises at least one of an infrared transmitter and a radio frequency transmitter.

18. The apparatus of claim 14, further comprising a verification device configured to verify that said target destination equals an actual destination of said medication container.

19. A method for tracking medications, said method comprising the steps of:
    placing medications within a receptacle, a tracking device being coupled to said receptacle;
    associating said tracking device with a target destination;
    delivering said medications to an actual destination;
    moving the tracking device from a first location to a second location on the receptacle;
    activating automatically said tracking device in response to the step of moving the tracking device; and
    verifying that said actual destination equals said target destination.

20. The method of claim 19, further comprising the step of logging transactional data regarding said actual destination of said medications.

21. The method of claim 20, further comprising the step of receiving a confirmation regarding said actual destination of said medications.

22. A method for tracking medications, said method comprising the steps of:
    providing medications at an initial location;
    tagging said medications;
    activating a tracking device coupled to said tagged medications;
    associating said tracking device with a target destination;
    tracking said tagged medications substantially continuously from said initial location to an actual destination; and
    verifying that said actual destination equals said target destination.

23. The method of claim 22, further comprising the step of logging transactional data regarding said actual destination of said medications.

24. The method of claim 23, further comprising the step of receiving a confirmation regarding said actual destination of said medications.

25. A system for tracking medications in a hospital, the system comprising:
    a controller;
    a receptacle configured to receive medications;
    a tracking device coupled to said receptacle and configured to communicate with said controller when the receptacle is moved to a destination;
    a switch operably coupled to said tracking device and configured to activate said tracking device automatically in response to movement of said tracking device relative to at least a portion of said receptacle; and
    means for associating said tracking device with a destination, and verifying said destination.

26. The system of claim 25, wherein the plurality of instructions, when executed by said controller, further cause said controller to log transactional data regarding at least one of said association and said verification.

27. The system of claim 25, wherein said means for associating includes a computer network.

28. The method of claim 19, wherein said receptacle comprises one of an intravenous bag and a container housing.

29. The method of claim 28, further comprising the step of moving said tracking device from a hanging hole of said intravenous bag to a solid web tab of said intravenous bag.

30. The method of claim 28, wherein said receptacle further comprises a lid supported by said container housing, and further comprising the step of moving said lid relative to said container housing.

31. The method of claim 22, wherein said step of tagging said medications comprises placing said medications within a receptacle.

32. The system of claim 25, wherein said receptacle comprises one of an intravenous bag and a container housing.

33. The system of claim 32, wherein said switch is configured to activate said tracking device when said tracking device moves from a hanging hole of said intravenous bag to a solid web tab of said intravenous bag.

34. The system of claim 32, wherein said receptacle further comprises a lid supported by said container housing, and said switch is configured to activate said tracking device when said lid moves relative to said container housing.

* * * * *